US00PP29124P3

(12) United States Plant Patent
Ash et al.

(10) Patent No.: US PP29,124 P3
(45) Date of Patent: Mar. 20, 2018

(54) PISTACHIO ROOTSTOCK NAMED 'UCB1-D154'

(50) Latin Name: ***Pistacia atlantica*×*Pistacia integerrima***
Varietal Denomination: UCB1-D154

(71) Applicants: John Scott Duarte, Modesto, CA (US); Jeffrey Thomas Duarte, Modesto, CA (US)

(72) Inventors: Kendall Ash, Hughson, CA (US); Javier Castillon, Hughson, CA (US); Dharam Sharma, Hughson, CA (US)

( * ) Notice: Subject to any disclaimer, the term of this patent is extended or adjusted under 35 U.S.C. 154(b) by 118 days.

(21) Appl. No.: 14/756,676

(22) Filed: Sep. 29, 2015

(65) Prior Publication Data

US 2017/0094852 P1 Mar. 30, 2017

(51) Int. Cl.
*A01H 5/00* (2006.01)

(52) U.S. Cl.
USPC ..... Plt./152

(58) Field of Classification Search
USPC ..... Plt./152
See application file for complete search history.

(56) References Cited

U.S. PATENT DOCUMENTS

| | | | |
|---|---|---|---|
| PP17,701 | P3 | 5/2007 | Parfitt et al. |
| PP17,758 | P2 | 5/2007 | Bradford |
| PP18,262 | P3 | 12/2007 | Parfitt et al. |
| PP26,915 | P3 | 7/2016 | MacIlvaine et al. |
| PP26,916 | P3 | 7/2016 | MacIlvaine et al. |
| PP27,079 | P3 | 8/2016 | Blackwell |
| PP27,318 | P3 | 11/2016 | MacIlvaine et al. |
| PP27,319 | P3 | 11/2016 | MacIlvaine et al. |
| PP27,436 | P3 | 12/2016 | MacIlvaine et al. |

OTHER PUBLICATIONS

Blake, Sanden et al, Large-Scale Utilization of Saline Groundwater for Irrigation of Pistachios Interplanted with Cotton (University of California 2009).
Ferguson, et al., Pistachio Production Manual, Fourth Edition 2005, Ch. 8, Pistachio Rootstocks (University of California 2005).

*Primary Examiner* — Susan McCormick Ewoldt
*Assistant Examiner* — Karen Redden
(74) *Attorney, Agent, or Firm* — Mark D. Miller

(57) ABSTRACT

Disclosed is a new and distinct variety of pistachio rootstock called 'UCB1-D154' characterized in that, when compared to the industry standard 'UCB1-D1' rootstock, it has greater growth and tolerance to the soil salts of calcium chloride, sodium sulfate, sodium carbonate and sodium bicarbonate; greater growth and tolerance to high levels of dissolved salts in irrigation water; and earlier vegetative bud break.

2 Drawing Sheets

Latin name: *Pistacia atlantica*×*Pistacia integerrima.*
Varietal denomination: 'UCB1-D154'.

CROSS-REFERENCES TO RELATED APPLICATIONS

The present variety was developed as part of a breeding program which produced the following pistachio rootstocks 'UCB1-D90' (Ser. No. 14/756,672), 'UCB1-D71' (Ser. No. 14/756,673), and 'UCB1-D110' (Ser. No. 14/756,675).

BACKGROUND OF THE NEW VARIETY

The present invention comprises a new and distinct cultivar of hybrid pistachio *Pistacia atlantica* (not patented)× *Pistacia integerrima* (not patented) used as a rootstock known by the varietal name 'UCB1-D154'. The variety 'UCB1-D154', is an in vitro, single selection of the segregating controlled cross of (*P. atlantica*×*P. integerrima*) made at Davis, Calif. The purpose of the selection program was to develop rootstocks with superior tolerance to soil salts. Seedlings were tested in salt trials in the laboratory and compared to the 'UCB1-D1' (not patented) rootstock. Those seedlings that exhibited high tolerance to various soil salts were selected. The new variety exhibits high tolerance to numerous, common salts found in the soil and irrigation water. The present variety has higher resistance to *Verticillium* disease than the female parent, *Pistacia atlantica*; and has higher cold tolerance than the male parent, *Pistacia integerrima.*

The following characteristics distinguish clone 'UCB1-D154' from the industry standard, 'UCB 1-D1' (not patented) rootstock:

1. Greater growth and tolerance to the soil salts, calcium chloride, sodium sulfate, sodium carbonate and sodium bicarbonate.
2. Greater growth and tolerance to high levels of dissolved salts in irrigation water.
3. Earlier vegetative bud break.
4. The present variety differs from rootstocks UCB1-D71, UCB1-D90, and UCB1-D110 in that the present variety is more tolerant to the soil salt sodium sulfate than the other three varieties and UCB1-D1 (not patented).

ORIGIN AND ASEXUAL REPRODUCTION OF THE NEW VARIETY

Asexual reproduction of the new and distinct variety of rootstock was accomplished by germinating seed in vitro under aseptic conditions and propagating the resulting seedlings using micropropagation techniques. Shoot epicotyl and hypocotyl tissue were collected from germinating seedlings and placed on a standard growth media to produce shoots. The shoots were sub-cultured and multiplied until desired numbers were obtained and then transferred to standard rooting media for rooting. Rooted plantlets were transferred to a peat:perlite media in acclimation chambers under 100% humidity. Field environmental parameters were gradually introduced to harden plantlets which were then successively transferred to larger pots in the greenhouse as their size increased. These potted trees were used to establish field performance trials. Subsequent evaluations have shown those asexual reproductions are true-to-type to the original rootstock selection. All characteristics of the original tree were established and appear to be transmitted completely through succeeding asexual propagations.

SUMMARY OF THE NEW VARIETY

The 'UCB1-D154' rootstock is characterized by its tolerance to high levels of the soil salts, calcium chloride, sodium sulfate, sodium carbonate and sodium bicarbonate. In each case clone 'UCB1-D154' had greater growth in laboratory salt trials than the industry standard rootstock, 'UCB1-D1' (not patented). In another laboratory salt trial, media was supplemented with the total salt load detected in saline San Joaquin Valley irrigation water and growth of clone 'UCB1-D154' outperformed that of 'UCB1-D1' (not patented) in the presence of these high levels of salts. In addition, vegetative bud break of 'UCB1-D154' was observed to be approximately 3 days earlier than 'UCB1-D1' (not patented).

DESCRIPTION OF THE ILLUSTRATIONS

The accompanying photographic illustrations show typical specimens of vegetative growth of the new variety, with the color being as nearly true as is possible with color illustrations of this type:

DESCRIPTION OF THE NEW VARIETY

Figure 1:
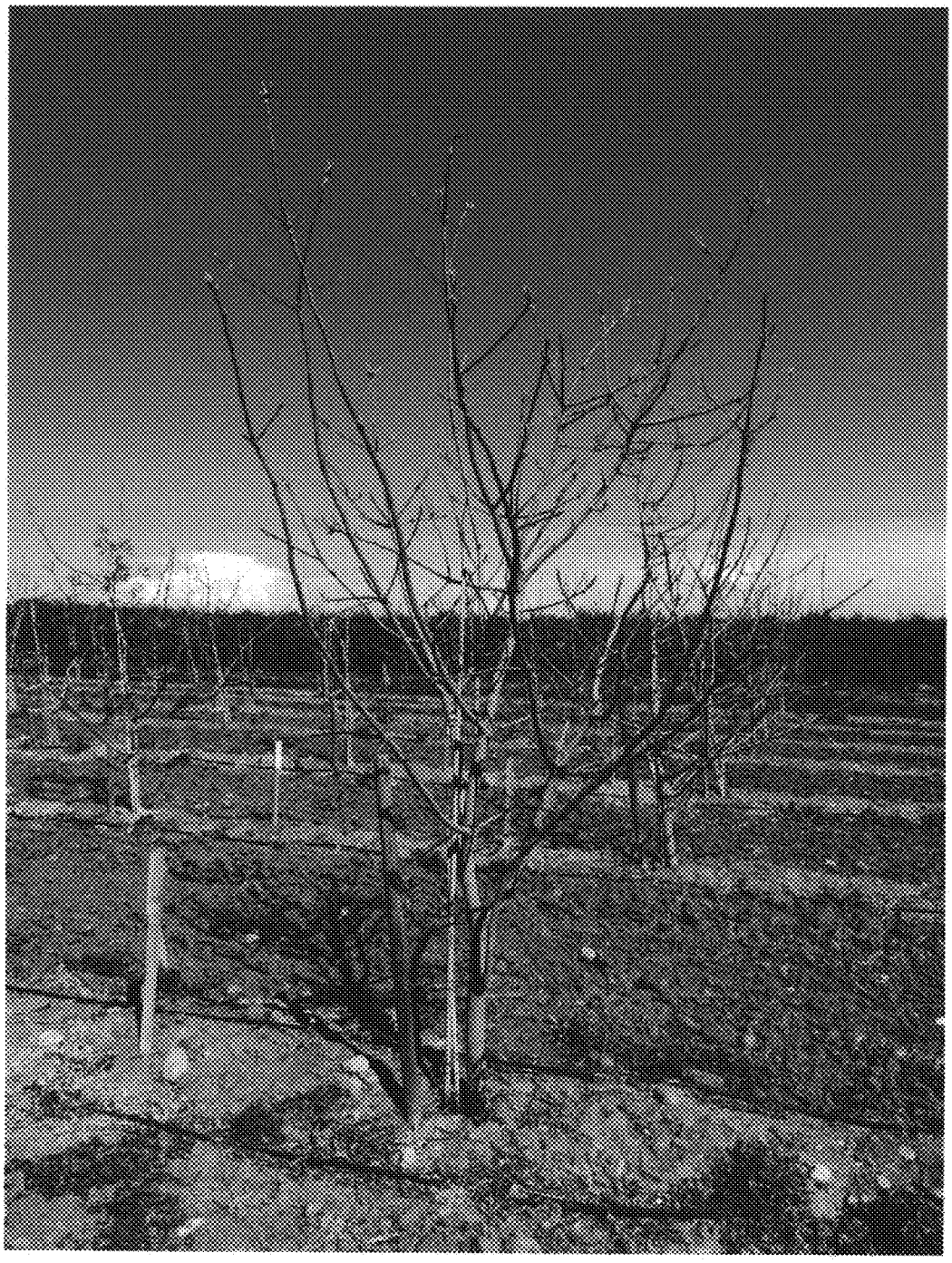
FIG. 1 shows a 4 year old pistachio tree of the new variety.
Figure 2:
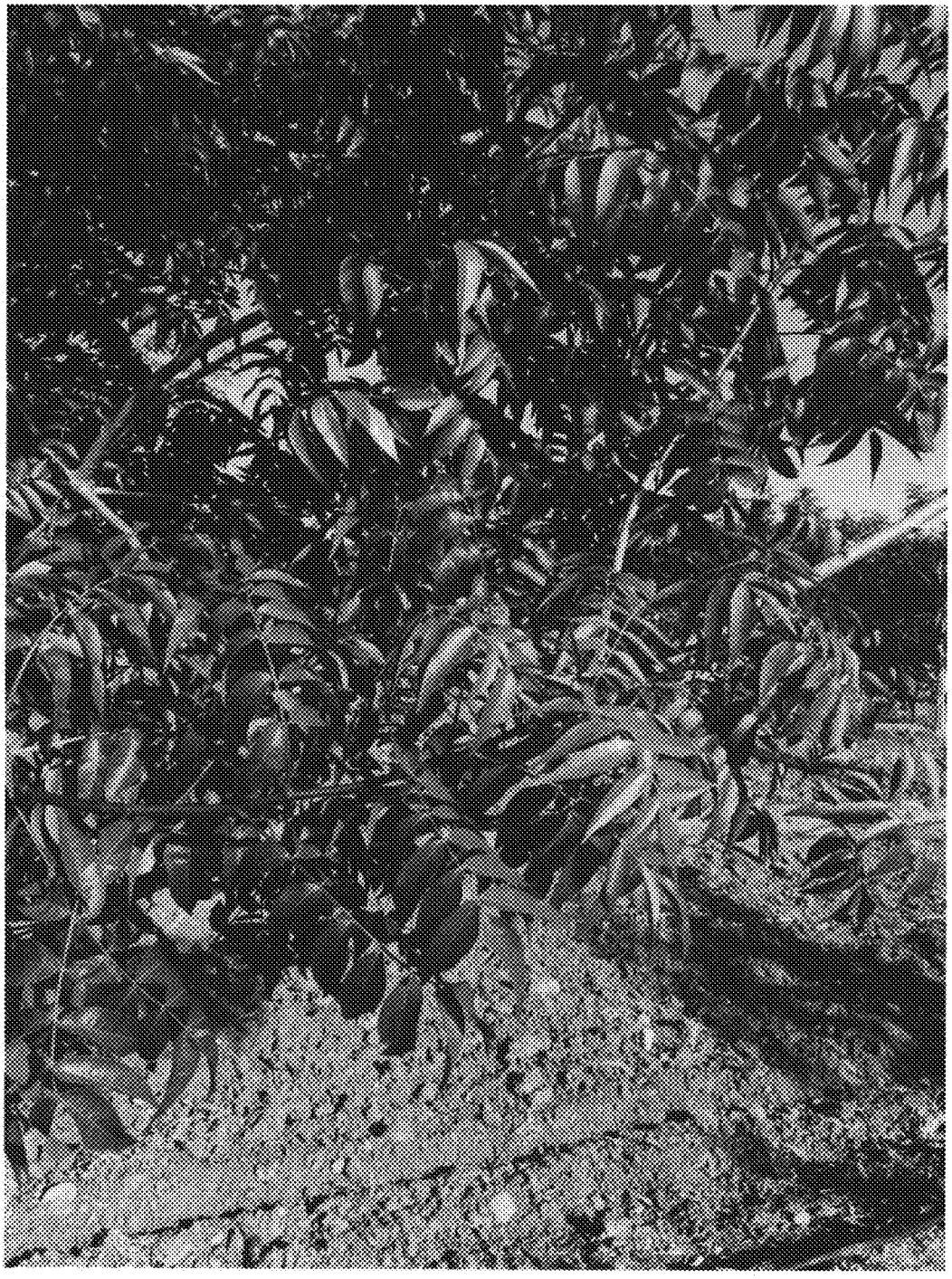
FIG. 2 shows a close-up of the mature leaves of the new variety.

The following detailed description sets forth the characteristics of the new variety. The data which defines these characteristics was collected under natural daylight on plants grown in the central valley of California in Stanislaus county in the greenhouse and in the field. Descriptions may vary in slight detail due to climatic, soil and cultural conditions under which the variety may be grown. Color designations are presented with reference to the Inter-Society Color Council, National Bureau of Standards, except where common color names are also included.

Tree: Trunk circumference 1 foot off the ground is 22.2 cm. Trunk lenticels are approximately 3.3 mm in length and 1.0 mm in width. Trunk lenticels are linear in shape. Trunk lenticel color is strong brown [55. s.B]. Bark color is dark grayish yellow [91. d.g.Y]. Trunk lenticels number approximately 30 per square inch. Branch lenticels are approximately 3.0 mm in length and 0.9 mm in width. Branch lenticels are linear in shape. Branch lenticel color is strong brown [55. s.B]. Branch lenticels number approximately 35 per square inch.

Vegetative buds:

*Size*.—Approximately 56 mm in length and 7 mm in width.

*Shape*.—Conical.

*Color*.—Brilliant, yellowish green [130. b.y.G] with strong, orange yellow [68. s.OY] exterior basal scales. As tips unfurl they become strong purplish red [255. s.p.R]. First vegetative buds of 'UCB1-D154' opened approximately 3 days earlier than 'UCB1-D1' (not patented). Leaflet blade color on the top and bottom surfaces is vivid red [11. v.R]. At the junction of the base of the petiole with the rachis, tissue color is brilliant, yellowish green [130. b.y.G]. Expanding rachis color is brilliant, yellowish green [130. b.y.G] at the extreme tip and very dark purplish red [260.v.d.p.R] on all sides elsewhere. Leaf venation pattern is pinnate and alternate. Midrib and veins are brilliant, yellowish green [130. b.y.G]. Compound leaves typically have between 9 and 11 leaflets.

Foliage: Leaves are pinnately compound composed of alternate leaflets numbering between 17 and 21. Compound leaf size variations are great but average approximately 57 cm in length and 48 cm in width at the widest point. Young leaflets are glossy and dark greyish red [20. d.g.R] on upper surfaces and moderate olive green [125. m.OG] on lower surfaces. Older leaflet surfaces are strong olive green [123. s.OG] on upper surfaces and moderate olive green [125. m.OG] on lower surfaces. Leaflet shape is lanceolate with an acute apex and cuneate base. There is great variation in leaf and leaflet size depending on the time of the season, position on the tree and tree age. Leaflet size varies considerably but averages 77 mm in length and 24 mm in width. Leaflet venation pattern is pinnate and venation is brilliant yellowish green [130. b.y.G]. The midrib is prominent and the same color as the venation pattern. Leaflet margins are entire and surfaces are glabrous. Petiole and rachis younger tissue upper and lower surface color is predominately strong purplish red [255. s.p.R] with some strong yellowish green [131. s.y.G] streaking on lower surfaces of older tissues. Petiole length varies considerably but averages 65 mm in length from point of rachis attachment to basal leaflet, and is glabrous with no wings. Rachis length varies considerably and averages about 42 cm in length.

Salt tolerance: Different concentrations of individual salts that contribute to soil salinity and alkalinity ranging from 0 to 10,000 mg/l were added to the culture medium that rootstock was growing in. Each clone-salt combination was replicated four times. Observations were taken on visual injury symptoms and growth measured by number of shoots and leaves per plant. Clone 'UCB1-D154' rootstock is characterized by its tolerance to high levels of the soil salts, calcium chloride (at 10,000 mg/l), sodium sulfate (at 10,000 mg/l), sodium carbonate (at 1,000 mg/l) and sodium bicarbonate (at 1,000 mg/l). As measured on a growth scale of 1 to 10, in the case of each of these salt trials clone 'UCB1-D154' had greater growth than the industry standard rootstock, 'UCB1-D1' (not patented). In another salt trial, media was supplemented with the comparable total salt load detected in saline San Joaquin Valley irrigation water (Sanden, B. et al. 2009. Large-Scale Utilization of Saline Groundwater for Irrigation of Pistachios Interplanted with Cotton. 2009 Progress Rpt. of California Pistachio Comm.) and growth of clone 'UCB1-D154' outperformed that of 'UCB1-D1' (not patented) in the presence of high soluble salts.

Disease/cold tolerance: The present variety has higher resistance to *Verticillium* disease than the female parent, *Pistacia atlantica*. The present variety has higher cold tolerance than the male parent, *Pistacia integerrima.*

Having thus described and illustrated the new variety of rootstock, what is claimed as new and desired to be secured by plant letters patent is:

1. A new and distinct variety of pistachio rootstock plant substantially as herein described and illustrated.

* * * * *